(12) United States Patent
Nelson et al.

(10) Patent No.: US 8,119,622 B2
(45) Date of Patent: *Feb. 21, 2012

(54) 7-PHENYL-SUBSTITUTED TETRACYCLINE COMPOUNDS

(75) Inventors: Mark L. Nelson, Norfolk, MA (US); Mohamed Y. Ismail, Bedford, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/635,423

(22) Filed: Dec. 10, 2009

(65) Prior Publication Data

US 2010/0160656 A1    Jun. 24, 2010

Related U.S. Application Data

(60) Division of application No. 12/183,711, filed on Jul. 31, 2008, now abandoned, which is a continuation of application No. 11/300,917, filed on Dec. 15, 2005, now abandoned, which is a continuation of application No. 10/853,536, filed on May 24, 2004, now abandoned, which is a continuation of application No. 09/883,137, filed on Jun. 15, 2001, now abandoned.

(60) Provisional application No. 60/212,030, filed on Jun. 16, 2000, provisional application No. 60/212,471, filed on Jun. 16, 2000.

(51) Int. Cl.
C07C 237/26    (2006.01)

(52) U.S. Cl. .......................... 514/203; 514/206

(58) Field of Classification Search .................. 552/203, 552/206
See application file for complete search history.

(56) References Cited

U.S. PATENT DOCUMENTS

| | | | |
|---|---|---|---|
| 2,980,584 A | 4/1961 | Hammer | |
| 2,990,331 A | 6/1961 | Horst et al. | |
| 3,007,965 A | 11/1961 | Growich, Jr. et al. | |
| 3,062,717 A | 11/1962 | Hammer | |
| 3,165,531 A | 1/1965 | Blackwood et al. | |
| 3,219,671 A | 11/1965 | Hlavka et al. | |
| 3,226,436 A | 12/1965 | Petisi et al. | |
| RE26,253 E | 8/1967 | Patisi et al. | |
| 3,338,963 A | 8/1967 | Petisi et al. | |
| RE26,271 E | 9/1967 | Boothe et al. | |
| 3,341,585 A | 9/1967 | Bitha et al. | |
| 3,345,379 A | 10/1967 | Martell et al. | |
| 3,345,410 A | 10/1967 | Winterbottom et al. | |
| 3,348,251 A | 10/1967 | Appleton et al. | |
| 3,360,561 A | 12/1967 | Zambrano | |
| 3,373,193 A | 3/1968 | Schroeder et al. | |
| 3,373,196 A | 3/1968 | Bitha et al. | |
| 3,397,230 A | 8/1968 | Winterbottom et al. | |
| 3,403,179 A | 9/1968 | Zambrano | |
| 3,454,697 A | 7/1969 | Joyner et al. | |
| 3,518,306 A | 6/1970 | Martell et al. | |
| 3,557,280 A | 1/1971 | Weber et al. | |
| 3,579,579 A | 5/1971 | Ross et al. | |
| 3,674,859 A | 7/1972 | Beutel et al. | |
| 3,901,942 A | 8/1975 | Bernardi et al. | |
| 3,957,980 A | 5/1976 | Noseworthy | |
| 4,018,889 A | 4/1977 | Armstrong | |
| 4,024,272 A | 5/1977 | Rogalski et al. | |
| 4,126,680 A | 11/1978 | Armstrong | |
| 5,021,407 A | 6/1991 | Levy | |
| 5,248,797 A | 9/1993 | Sum | |
| 5,258,372 A | 11/1993 | Levy | |
| 5,281,628 A | 1/1994 | Hlavka et al. | |
| 5,284,963 A | 2/1994 | Sum et al. | |
| 5,322,278 A | 6/1994 | Jeanrot | |
| 5,326,759 A | 7/1994 | Hlavka et al. | |
| 5,328,902 A | 7/1994 | Sum et al. | |
| 5,371,076 A | 12/1994 | Lee et al. | |
| 5,380,888 A | 1/1995 | Sum et al. | |
| 5,386,041 A | 1/1995 | Sum et al. | |
| 5,401,729 A | 3/1995 | Sum et al. | |
| 5,401,863 A | 3/1995 | Hlavka et al. | |
| 5,420,272 A | 5/1995 | Sum et al. | |
| 5,430,162 A | 7/1995 | Sum et al. | |
| 5,442,059 A | 8/1995 | Sum et al. | |
| 5,457,096 A | 10/1995 | Sum et al. | |
| 5,466,684 A | 11/1995 | Sum et al. | |
| 5,494,903 A | 2/1996 | Hlavka et al. | |
| 5,495,018 A | 2/1996 | Sum et al. | |
| 5,495,030 A | 2/1996 | Sum et al. | |

(Continued)

FOREIGN PATENT DOCUMENTS

WO    WO-0028983 A1    5/2000

(Continued)

OTHER PUBLICATIONS

Koza, "Synthesis of 7-substituted tetracycline derivatives". Organic Letters, vol. 2(6), pp. 815-817, Mar. 1, 2000.*

(Continued)

*Primary Examiner* — Barbara P Badio
(74) *Attorney, Agent, or Firm* — Mintz Levin Cohn Ferris Glovsky and Popeo, P.C.; Heidi A. Erlacher

(57) ABSTRACT

7-phenyl-substituted tetracycline compounds which are substantially free of positional isomers, methods of treating tetracycline responsive states, and pharmaceutical compositions containing the 7-phenyl-substituted tetracycline compounds are described. 7-substituted tetracycline compounds which are substantially free of positional isomers, methods of treating tetracycline responsive states, and pharmaceutical compositions containing the 7-substituted tetracycline compounds are described.

15 Claims, No Drawings

U.S. PATENT DOCUMENTS

| | | | |
|---|---|---|---|
| 5,495,031 | A | 2/1996 | Sum et al. |
| 5,512,553 | A | 4/1996 | Sum et al. |
| 5,529,990 | A | 6/1996 | Hlavka et al. |
| 5,530,117 | A | 6/1996 | Hlavka et al. |
| 5,567,692 | A | 10/1996 | Sum et al. |
| 5,639,742 | A | 6/1997 | Lee et al. |
| 5,675,030 | A | 10/1997 | Krishnan et al. |
| 5,789,395 | A | 8/1998 | Amin et al. |
| 5,834,450 | A | 11/1998 | Su |
| 5,886,175 | A | 3/1999 | Sum et al. |
| 6,500,812 | B2 | 12/2002 | Nelson et al. |
| 6,506,740 | B1 | 1/2003 | Ashley et al. |
| 6,617,318 | B1 | 9/2003 | Nelson et al. |
| 6,624,168 | B2 | 9/2003 | Nelson et al. |
| 6,642,270 | B2 * | 11/2003 | Nelson et al. ............ 514/464 |
| 6,683,068 | B2 | 1/2004 | Nelson et al. |
| 6,818,634 | B2 | 11/2004 | Nelson et al. |
| 6,818,635 | B2 | 11/2004 | Nelson et al. |
| 6,833,365 | B2 | 12/2004 | Levy et al. |
| 6,841,546 | B2 | 1/2005 | Draper et al. |
| 6,846,939 | B2 | 1/2005 | Nelson et al. |
| 6,849,615 | B2 | 2/2005 | Nelson et al. |
| 7,001,918 | B2 | 2/2006 | Huss et al. |
| 7,045,507 | B2 | 5/2006 | Draper et al. |
| 7,056,902 | B2 | 6/2006 | Nelson et al. |
| 7,067,681 | B2 | 6/2006 | Nelson et al. |
| 7,094,806 | B2 | 8/2006 | Nelson et al. |
| 7,202,035 | B2 | 4/2007 | Squires et al. |
| 2002/0103171 | A1 | 8/2002 | Nelson et al. |
| 2002/0111335 | A1 | 8/2002 | Nelson et al. |
| 2002/0115644 | A1 | 8/2002 | Levy et al. |
| 2002/0128237 | A1 | 9/2002 | Nelson et al. |
| 2002/0128238 | A1 | 9/2002 | Nelson et al. |
| 2002/0193354 | A1 | 12/2002 | Nelson et al. |
| 2003/0100017 | A1 | 5/2003 | Draper et al. |
| 2003/0125348 | A1 | 7/2003 | Nelson et al. |
| 2003/0166585 | A1 | 9/2003 | Draper et al. |
| 2004/0015267 | A1 | 1/2004 | Sait et al. |
| 2004/0033996 | A1 | 2/2004 | Nelson et al. |
| 2004/0048835 | A1 | 3/2004 | Nelson et al. |
| 2004/0063674 | A1 | 4/2004 | Levy et al. |
| 2004/0092490 | A1 | 5/2004 | Draper et al. |
| 2004/0138183 | A1 | 7/2004 | Nelson et al. |
| 2004/0176334 | A1 | 9/2004 | Nelson et al. |
| 2004/0192657 | A1 | 9/2004 | Garcia-Luzon et al. |
| 2004/0214800 | A1 | 10/2004 | Levy et al. |
| 2004/0242548 | A1 | 12/2004 | Draper et al. |
| 2004/0266740 | A1 | 12/2004 | Huss et al. |
| 2005/0020545 | A1 | 1/2005 | Draper et al. |
| 2005/0026875 | A1 | 2/2005 | Nelson et al. |
| 2005/0026876 | A1 | 2/2005 | Nelson et al. |
| 2005/0038002 | A1 | 2/2005 | Nelson et al. |
| 2005/0070510 | A1 | 3/2005 | Draper et al. |
| 2005/0119235 | A1 | 6/2005 | Nelson et al. |
| 2005/0137174 | A1 | 6/2005 | Ohemeng et al. |
| 2005/0143352 | A1 | 6/2005 | Nelson et al. |
| 2005/0143353 | A1 | 6/2005 | Nelson et al. |
| 2005/0148551 | A1 | 7/2005 | Nelson et al. |
| 2005/0187198 | A1 | 8/2005 | Nelson et al. |
| 2005/0215532 | A1 | 9/2005 | Levy et al. |
| 2005/0250744 | A1 | 11/2005 | Levy et al. |
| 2005/0288262 | A1 | 12/2005 | Bandarage et al. |
| 2006/0003971 | A1 | 1/2006 | Nelson |
| 2006/0008463 | A1 | 1/2006 | Itoh et al. |
| 2006/0008933 | A1 | 1/2006 | Muller et al. |
| 2006/0084634 | A1 | 4/2006 | Huss et al. |
| 2006/0089336 | A1 | 4/2006 | Nelson et al. |
| 2006/0148765 | A1 | 7/2006 | Nelson et al. |
| 2006/0166944 | A1 | 7/2006 | Berniac et al. |
| 2006/0166945 | A1 | 7/2006 | Abato et al. |
| 2006/0166946 | A1 | 7/2006 | Nelson et al. |
| 2006/0194773 | A1 | 8/2006 | Levy et al. |
| 2006/0205698 | A1 | 9/2006 | Nelson et al. |
| 2007/0167415 | A1 | 7/2007 | Levy et al. |

FOREIGN PATENT DOCUMENTS

| | | |
|---|---|---|
| WO | WO-0119784 A1 | 3/2001 |
| WO | WO-0187824 A2 | 11/2001 |
| WO | WO-0198259 A1 | 12/2001 |
| WO | WO-0204407 A2 | 1/2002 |

OTHER PUBLICATIONS

Koza, Darrell J. "Synthesis of 7-Substituted Tetracycline Derivatives," Organic Letters, vol. 2(6): 815-817 (2000).

* cited by examiner

7-PHENYL-SUBSTITUTED TETRACYCLINE COMPOUNDS

RELATED APPLICATIONS

This application is a divisional of U.S. patent application Ser. No. 12/183,711, filed Jul. 31, 2008, now abandoned; which is a continuation of U.S. patent application Ser. No. 11/300,917, filed Dec. 15, 2005, now abandoned; which is a continuation of U.S. patent application Ser. No. 10/853,536, filed May 24, 2004, now abandoned; which is a continuation of U.S. patent application Ser. No. 09/883,137, filed Jun. 15, 2001, now abandoned; which claims the benefit of U.S. Provisional Application Ser. No. 60/212,030, filed Jun. 16, 2000, and U.S. Provisional Application Ser. No. 60/212,471, filed Jun. 16, 2000; the entire contents of each of the aforementioned applications are hereby incorporated by reference.

BACKGROUND OF THE INVENTION

The development of the tetracycline antibiotics was the direct result of a systematic screening of soil specimens collected from many parts of the world for evidence of microorganisms capable of producing bacteriocidal and/or bacteriostatic compositions. The first of these novel compounds was introduced in 1948 under the name chlortetracycline. Two years later, oxytetracycline became available. The elucidation of the chemical structure of these compounds confirmed their similarity and furnished the analytical basis for the production of a third member of this group in 1952, tetracycline. A new family of tetracycline compounds, without the ring-attached methyl group present in earlier tetracyclines, was prepared in 1957 and became publicly available in 1967; and minocycline was in use by 1972.

Recently, research efforts have focused on developing new tetracycline antibiotic compositions effective under varying therapeutic conditions and routes of administration. New tetracycline analogues have also been investigated which may prove to be equal to or more effective than the originally introduced tetracycline compounds. Examples include U.S. Pat. Nos. 3,957,980; 3,674,859; 2,980,584; 2,990,331; 3,062,717; 3,557,280; 4,018,889; 4,024,272; 4,126,680; 3,454,697; and 3,165,531. These patents are representative of the range of pharmaceutically active tetracycline and tetracycline analogue compositions.

Historically, soon after their initial development and introduction, the tetracyclines were found to be highly effective pharmacologically against rickettsiae; a number of gram-positive and gram-negative bacteria; and the agents responsible for lymphogranuloma venereum, inclusion conjunctivitis, and psittacosis. Hence, tetracyclines became known as "broad spectrum" antibiotics. With the subsequent establishment of their in vitro antimicrobial activity, effectiveness in experimental infections, and pharmacological properties, the tetracyclines as a class rapidly became widely used for therapeutic purposes. However, this widespread use of tetracyclines for both major and minor illnesses and diseases led directly to the emergence of resistance to these antibiotics even among highly susceptible bacterial species both commensal and pathogenic (e.g., pneumococci and *Salmonella*). The rise of tetracycline-resistant organisms has resulted in a general decline in use of tetracyclines and tetracycline resistant organisms has resulted in a general decline in use of tetracyclines and tetracycline analogue compositions as antibiotics of choice.

SUMMARY OF THE INVENTION

The invention pertains to 7-substituted tetracycline compounds which are substantially free of positional isomers. The compounds have the formula:

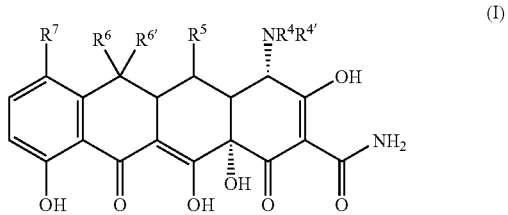

wherein:

$R^4$ and $R^{4'}$ are each alkyl;

$R^5$ is hydrogen, hydroxyl, or a prodrug moiety;

$R^6$ and $R^{6'}$ are each independently hydrogen, hydroxyl, alkyl, or taken together, alkenyl;

$R^7$ is halo substituted, a N-substituted phenyl, or an unsubstituted phenyl; and pharmaceutically acceptable salts thereof.

In another embodiment, $R^7$ is mono-, di-, or tri-halo substituted phenyl. In another embodiment, $R^7$ is 2-halo substituted phenyl. In yet another embodiment, $R^7$ is 3-halo substituted phenyl. In a further embodiment, $R^7$ is 4-halo substituted phenyl. In another embodiment, $R^7$ is a 2, 3 or 4-N-substituted phenyl.

A method is provided for preparing tetracycline compounds of the invention having a desired purity, e.g., such that the desired compound is provided in a manner substantially free of positional isomers. In a preferred embodiment, a 7-halo substituted sancycline compound, from which the tetracycline compounds of the invention may be prepared, is provided which enables the production of the desired compound in a manner substantially free of positional isomers. In a further preferred embodiment, the desired tetracycline compound is at least 75%, 80%, 85%, 90%, 95% or 100% free of positional isomers. These desired compounds may be used in methods of treating tetracycline responsive states, and pharmaceutical compositions, as substantially set forth herein.

The invention also pertains to a method for treating a tetracycline responsive state in a mammal, by administering to a mammal a compound of formula I substantially free of positional isomers. In another aspect, the invention relates to the use of a compound of formula I which is substantially free of positional isomers to treat a tetracycline responsive state. The invention also pertains to pharmaceutical compositions comprising a compound of formula I which is substantially free of positional isomers, and to the use of a compound of formula I which is substantially free of positional isomers in the manufacture of a medicament to treat a tetracycline responsive state.

DETAILED DESCRIPTION OF THE INVENTION

The invention pertains to 7-substituted tetracycline compounds which are substantially free of positional isomers. The compounds have the formula:

(I)

[Structure of Formula I: tetracycline core with substituents R⁷, R⁶, R⁶', R⁵, NR⁴R⁴', OH, NH₂, and OH, O, OH, O positions]

wherein:

$R^4$ and $R^{4'}$ are each alkyl;

$R^5$ is hydrogen, hydroxyl, or a prodrug moiety;

$R^6$ and $R^{6'}$ are each independently hydrogen, hydroxyl, alkyl, or taken together, alkenyl;

$R^7$ is halo substituted, N-substituted phenyl or unsubstituted phenyl; and pharmaceutically acceptable salts thereof.

In another embodiment, $R^7$ is mono-, di-, or tri-halo substituted phenyl. In another embodiment, $R^7$ is 2-halo substituted phenyl. In yet another embodiment, $R^7$ is 3-halo substituted phenyl. In a further embodiment, $R^7$ is 4-halo substituted phenyl.

In another further embodiment, $R^7$ is a 2, 3 or 4-N-substituted phenyl, e.g., 7-(2-aminophenyl) sancycline, 7-(2-nitrophenyl) sancycline, 7-(2-N,N,-dimethylaminophenyl) sancycline, 7-(2-N,N,-diethylaminophenyl) sancycline, 7-(2-N,N,-dipropylaminophenyl) sancycline, 7-(2-N,N,-dibutylaminophenyl) sancycline, 7-(3-aminophenyl) sancycline, 7-(3-aminophenyl) sancycline, 7-(3-N,N,-dimethylaminophenyl) sancycline, 7-(3-N,N,-diethylaminophenyl) sancycline, 7-(3-N,N,-dipropylaminophenyl) sancycline, 7-(3-N,N,-dibutylaminophenyl) sancycline, 7-(4-aminophenyl) sancycline, 7-(4-nitrophenyl) sancycline, 7-(4-N,N,-dimethylaminophenyl) sancycline, 7-(4-N,N,-diethylaminophenyl) sancycline, 7-(4-N,N,-dipropylaminophenyl) sancycline, or 7-(4-N,N,-dibutylaminophenyl) sancycline, where said compounds are substantially free of positional isomers.

The term "tetracycline compound" includes compounds with a similar ring structure to tetracycline, such as those included in formula I. Some examples of tetracycline compounds which can be modified to include a substituent at position 7 include tetracycline, oxytetracycline, demeclocycline, methacycline, sancycline, and doxycycline; however, other derivatives and analogues comprising a similar ring structure are also included. Table 1 depicts tetracycline and several known tetracycline derivatives.

TABLE I

[Structure of Tetracycline]

Tetracycline

TABLE I-continued

[Structure of Oxytetracycline]

Oxytetracycline

[Structure of Demeclocycline]

Demeclocycline

[Structure of Methacycline]

Methacycline

[Structure of Doxycycline]

Doxycycline

[Structure of Chlorotetracycline]

Chlorotetracycline

[Structure of Minocycline]

Minocycline

The term "7-substituted tetracycline compounds" includes tetracycline compounds with a substituent at the 7 position. In an embodiment, the substituted tetracycline compound is substituted tetracycline (e.g., wherein $R^4$ and $R^{4'}$ are methyl, $R^5$ is hydrogen, $R^6$ is methyl and $R^{6'}$ is hydroxyl); substituted doxycycline (e.g., wherein $R^4$ and $R^{4'}$ are methyl, $R^5$ is hydroxyl $R^6$ is methyl and $R^{6'}$ is hydrogen); or substituted sancycline (wherein $R^4$ and $R^{4'}$ are methyl; $R^5$ is hydrogen and $R^6$ and $R^{6'}$ are hydrogen atoms). In another embodiment, the compound is a derivative of tetracycline, sancycline, doxycycline, oxytetracycline, or methacycline. In one embodiment, $R^5$, $R^6$ and $R^{6'}$ are each hydrogen and $R^4$ and $R^{4'}$ are each methyl.

In yet another further embodiment, $R^7$ is unsubstituted phenyl. Examples of tetracycline compounds with this $R^7$ substituent include 7-phenyl sancycline and 7,9 diphenylsancycline, where said compounds are substantially free of positional isomers.

In yet another embodiment, $R^7$ is halo substituted phenyl. The halo substituent can be, for example, chlorine, fluorine, bromine, or iodine, as well as mono-, di- or tri-halo substituted lower alkyl group, e.g., mono-, di- or tri-halo substituted methyl. In certain embodiments, the halo substitution of the phenyl substituent enhances the ability of the tetracycline compound to perform its intended function, e.g., treat tetracycline responsive states.

In a further embodiment, $R^7$ is mono-, di-, or tri-halo substituted phenyl. In certain embodiments, the 7-substituted tetracycline compound is 7-(2,4-difluorophenyl) sancycline, 7-(2,4-dichlorophenyl) sancycline, 7-(2,4-dibromophenyl) sancycline, or 7-(2,4-diiodophenyl) sancycline. In other embodiments, the 7-substituted tetracycline compound is 742,6-difluorophenyl) sancycline, 7-(2,6-dichlorophenyl) sancycline, 7-(2,6-dibromophenyl) sancycline, or 7-(2,6-diiodophenyl) sancycline, where said compounds are substantially free of positional isomers.

In another embodiment, $R^7$ is 2-halo substituted phenyl, e.g., 7-(2-fluorophenyl) sancycline, 7-(2-chlorophenyl) sancycline, 7-(2-bromophenyl) sancycline, or 7-(2-iodophenyl) sancycline, where said compounds are substantially free of positional isomers.

In yet another embodiment, $R^7$ is 3-halo substituted phenyl, e.g., 7-(3-fluorophenyl) sancycline, 7-(3-chlorophenyl) sancycline, 7-(3-bromophenyl) sancycline, or 7-(3-iodophenyl) sancycline, where said compounds are substantially free of positional isomers.

In further embodiment, $R^7$ is 4-halo substituted phenyl, e.g., 7-(4-fluorophenyl) sancycline, 7-(4-chlorophenyl) sancycline, 7-(4-bromophenyl) sancycline, or 7-(4-iodophenyl) sancycline, where said compounds are substantially free of positional isomers.

In yet another embodiment, $R^7$ is a mono-, di-, or tri-substituted phenyl where the substituent is a mono-, di- or tri-halo substituted lower alkyl group, e.g., mono-, di- or tri-halo substituted methyl. For example, the compound may be 7-(4-trichloromethylphenyl) sancycline, 7-(4-trifluoromethylphenyl) sancycline, 7-(4-tribromomethylphenyl) sancycline, or 7-(4-triiodomethylphenyl) sancycline, where said compounds are substantially free of positional isomers.

The term "N-substituted phenyl" includes phenyl substituted with one or more substituents with a nitrogen atom such as, but not limited to, nitro, amino, alkyl amino, and dialkylamino (e.g., dimethyl amino, diethylamino, dipropyl amino, dibutyl amino). The N-substituent may be at the 2, 3, 4, 5, or 6 position of the phenyl ring.

In another embodiment, $R^7$ is a 2-N-substituted phenyl, including 7-(2-aminophenyl) sancycline, 7-(2-nitrophenyl) sancycline, 7-(2-N,N,-dimethylaminophenyl) sancycline, 7-(2-N,N,-diethylaminophenyl) sancycline, 7-(2-N,N,-dipropylaminophenyl) sancycline, and 7-(2-N,N,-dibutylaminophenyl) sancycline, where said compounds are substantially free of positional isomers.

In another embodiment, $R^7$ is a 3-N-substituted phenyl, including 7-(3-aminophenyl) sancycline, 7-(3-nitrophenyl) sancycline, 7-(3-N,N,-dimethylaminophenyl) sancycline, 7-(3-.N,N,-diethylaminophenyl) sancycline, 7-(3-N,N,-dipropylaminophenyl) sancycline, and 7-(3-N,N,-dibutylaminophenyl) sancycline, where said compounds are substantially free of positional isomers.

In another embodiment, $R^7$ is 4-N-substituted phenyl, including 7-(4-aminophenyl) sancycline, 7-(4-nitrophenyl) sancycline, 7-(4-N,N,-dimethylaminophenyl) sancycline, 7-(4-N,N,-diethylaminophenyl) sancycline, 7-(4-N,N,-dipropylaminophenyl) sancycline, and 7-(4-N,N,-dibutylaminophenyl) sancycline, where said compounds are substantially free of positional isomers.

The 7-substituted compounds of the invention can be synthesized by methods known in the art and/or as described herein. In Scheme 1, a general synthetic scheme is outlined using a Suzuki coupling of a boronic acid with an iodo sancycline compound. Although the reaction is shown for sancycline, a similar procedure can be used for other tetracycline compounds. Furthermore, other aryl coupling reactions known in the art may also be used.

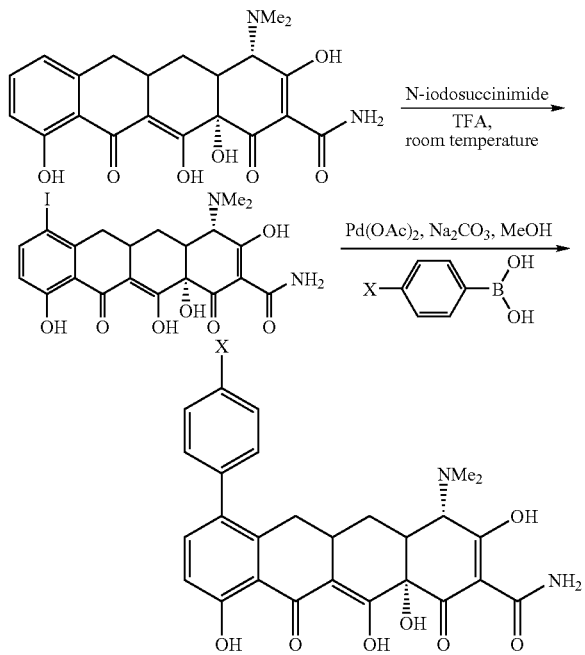

As shown in Scheme 1, an iodosancycline compound can be synthesized from unsubstituted sancycline by treating it with at least one equivalent N-iodosuccinimide (NIS) under acidic conditions. When sancycline was treated with NIS in trifluoroacetic acid, the reaction was carried out initially at 0° C., before being warmed to room temperature for five hours. The reaction is then quenched, and the resulting 7-iodosancycline can then be purified using standard techniques known in the art. The 7-iodosancycline can then be further reacted with a boronic acid, as shown in Scheme 1. 7-iodosancycline, a palladium catalyst (such as Pd(OAc)$_2$), is dissolved in a solvent and treated with aqueous sodium carbonate, and the boronic acid. The resulting compound can then be purified using techniques known in the art such as preparative HPLC and characterized.

The compounds of the invention can also be synthesized using Stille cross couplings Stille cross couplings can be performed using an appropriate tin reagent (e.g., R—SnBu$_3$) and a halogenated tetracycline compound, (e.g., 7-iodosancycline). The tin reagent and the iodotetracycline compound can be treated with a palladium catalyst (e.g., Pd(PPh$_3$)$_2$Cl$_2$ or Pd(AsPh$_3$)$_2$Cl$_2$) and, optionally, with an additional copper salt, e.g., CuI. The resulting compound can then be purified using techniques known in the art. The synthesis of the compounds of the invention are described in more detail in Example 1.

The language "a compound which is substantially free of positional isomers" includes a compound which has been isolated and/or purified from its positional isomers such that the desired compound is present in an amount acceptable for pharmaceutical purposes, e.g., at least 75 percent. The percent purity can be determined using art-recognized techniques. As set forth in exemplary fashion below, a method is provided for preparing tetracycline compounds of the invention having a desired purity, e.g., such that the desired compound is provided in a manner substantially free of positional isomers. In a preferred embodiment, a 7-halo substituted sancycline compound, from which the tetracycline compounds of the invention may be prepared, is provided which enables the production of the desired compound in a manner substantially free of positional isomers. In a further preferred embodiment, the desired tetracycline compound thus produced is at least 75%, 80%, 85%, 90%, 95% or 100% free of positional isomers.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl; cyclooctyl), alkyl substituted cycloalkyl groups, and cycloalkyl substituted alkyl groups. The term alkyl further includes alkyl groups, which comprise oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, the term, alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). The term "alkyl" also includes the side chains of natural and unnatural amino acids.

The term "aryl" includes groups with aromaticity, including 5- and 6-membered single-ring aromatic groups that may include from zero to four heteroatoms as well as multicyclic systems with at least one aromatic ring. Examples of aryl groups include benzene, phenyl, pyrrole, furan, thiophene, thiazole, isothiazole, imidazole, triazole, tetrazole, pyrazole, oxazole, isoxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as: for, example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or, an aromatic or heteroaromatic moiety. Aryl groups can also be fused or bridged with alicyclic or heterocyclic rings which are not aromatic so as to form a multicyclic system (e.g., tetralin, methylenedioxyphenyl).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "acyl" includes compounds and moieties which contain the acyl radical (CH3CO—) or a carbonyl group. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes compounds where a nitrogen atom is covalently bonded to at least one carbon or heteroatom. The term "alkylamino" includes groups and compounds wherein the nitrogen is bound to at least one additional alkyl group. The term "dialkylamino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide" or "aminocarboxy" includes compounds or moieties which contain a nitrogen atom which is bound to the carbon of a carbonyl or a thiocarbonyl group. The term includes "alkaminocarboxy" groups which include alkyl, alkenyl, or alkynyl groups bound to an amino group bound to a carboxy group. It includes arylaminocarboxy groups which include aryl or heteroaryl moieties bound to an amino group which is bound to the carbon of a carbonyl or thiocarbonyl group. The terms "alkylaminocarboxy," "alkenylaminocarboxy," "alkynylaminocarboxy," and "arylaminocarboxy" include moieties wherein alkyl, alkenyl, alkynyl and aryl moieties, respectively, are bound to a nitrogen atom which is in turn bound to the carbon of a carbonyl group.

The term "carbonyl" or "carboxy" includes compounds and moieties which contain a carbon connected with a double bond to an oxygen atom. Examples of moieties which contain a carbonyl include aldehydes, ketones, carboxylic acids, amides, esters, anhydrides, etc.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl"

which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O$^-$.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings. Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminocarbonyl, aralkylaminocarbonyl, alkenylaminocarbonyl, alkylcarbonyl, arylcarbonyl, aralkylcarbonyl, alkenylcarbonyl, aminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Examples of heteroatoms include nitrogen, oxygen, sulfur and phosphorus.

It will be noted that the structure of some of the compounds of this invention includes asymmetric carbon atoms. It is to be understood accordingly that the isomers arising from such asymmetry (e.g.; all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

Prodrugs are compounds which are converted in vivo to active forms (see, e.g., R. B. Silverman, 1992, "The Organic Chemistry of Drug Design and Drug Action", Academic Press, Chp. 8). Prodrugs can be used to alter the biodistribution (e.g., to allow compounds which would not typically enter the reactive site of the protease) or the pharmacokinetics for a particular compound. For example, a hydroxyl group, can be esterified, e.g., with a carboxylic acid group to yield an ester. When the ester is administered to a subject, the ester is cleaved, enzymatically or non-enzymatically, reductively or hydrolytically, to reveal the hydroxyl group.

The term "prodrug moiety" includes moieties which can be metabolized in vivo to a hydroxyl group and moieties which may advantageously remain esterified in vivo. Preferably, the prodrugs moieties are metabolized in vivo by esterases or by other mechanisms to hydroxyl groups or other advantageous groups. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionic acid esters and acyl esters.

The invention also features a method for treating a tetracycline compound responsive state in a subject, by administering to the subject a 7-substituted tetracycline compound of the invention, e.g., a compound of formula I which is substantially free of positional isomers. Preferably, an effective amount of the tetracycline compound which is substantially free of positional isomers is administered. Examples of 7-substituted tetracycline compounds of the invention include 7-phenyl sancycline, 7,9 diphenylsancycline, 7-(2-fluorophenyl) sancycline, 7-(2-chlorophenyl) sancycline, 7-(2-bromophenyl) sancycline, 7-(2-iodophenyl) sancycline, 7-(3-fluorophenyl) sancycline, 7-(3-chlorophenyl) sancycline, 7-(3-bromophenyl) sancycline, 7-(3-iodophenyl) sancycline, 7-(4-fluorophenyl) sancycline, 7-(4-chlorophenyl) sancycline, 7-(4-bromophenyl) sancycline, 7-(4-iodophenyl) sancycline, 7-(4-trichloromethylphenyl) sancycline, 7-(4-trifluoromethylphenyl) sancycline, 7-(4-tribromomethylphenyl) sancycline, 7-(4-triiodomethylphenyl) sancycline, 7-(2-aminophenyl) sancycline, 7-(2-nitrophenyl) sancycline, 7-(2-N,N,-dimethylaminophenyl) sancycline, 7-(2-N,N,-diethylaminophenyl) sancycline, 7-(2-N,N,-dipropylaminophenyl) sancycline, 7-(2-N,N,-dibutylaminophenyl) sancycline, 7-(3-aminophenyl) sancycline, 7-(3-nitrophenyl) sancycline, 7-(3-N,N,-dimethylaminophenyl) sancycline, 7-(3-N,N,-diethylaminophenyl) sancycline, 7-(3-N,N,-dipropylaminophenyl) sancycline, 7-(3-N,N,-dibutylaminophenyl) sancycline, 7-(4-aminophenyl) sancycline, 7-(4-nitrophenyl) sancycline, 7-(4-N,N,-dimethylaminophenyl) sancycline, 7-(4-N,N,-diethylaminophenyl) sancycline, 7-(4-N,N,-dipropylaminophenyl) sancycline, and 7-(4-N,N,-dibutylaminophenyl) sancycline, where said compounds are substantially free of positional isomers.

The language "tetracycline compound responsive state" includes states which can be treated, prevented, or otherwise ameliorated by the administration of a tetracycline compound of the invention. Tetracycline compound responsive states include bacterial infections (including those which are resistant to other tetracycline compounds), cancer, diabetes, and other states for which tetracycline compounds have been found to be active (see, for example, U.S. Pat. Nos. 5,789,395; 5,834,450; and 5,532,227). Compounds of the invention can be used to prevent or control important mammalian and veterinary diseases such as diarrhea, urinary tract infections, infections of skin and skin structure, ear, nose and throat infections, wound infection, mastitis and the like. In addition, methods for treating neoplasms using tetracycline compounds of the invention are also included (van der Bozert et al., *Cancer Res.*, 48:6686-6690 (1988)).

Bacterial infections may be caused by a wide variety of gram positive and gram negative bacteria. The compounds of the invention are useful as antibiotics against organisms which are resistant to other tetracycline compounds. The antibiotic activity of the tetracycline compounds of the invention may be determined using the method discussed in Example 2, or by using the in vitro standard broth dilution method described in Waitz, J. A., *National Commission for Clinical Laboratory Standards, Document* M7-A2, vol. 10, no. 8, pp. 13-20, $2^{nd}$ edition, Villanova, Pa. (1990).

The tetracycline compounds may also be used to treat infections traditionally treated with tetracycline compounds such as, for example, rickettsiae; a number of gram-positive and &am-negative bacteria; and the agents responsible for lymphogranuloma venereum, inclusion conjunctivitis, psittacosis. The tetracycline compounds may be used to treat infections of, e.g., *K. pneumoniae, Salmonella, E. hirae, A. baumanii, B. catarrhalis, H. influenzae, P. aeruginosa, E. faecium, E. coli, S. aureus* or. *E. faecalis*. In one embodiment, the tetracycline compound is used to treat a bacterial infection that is resistant to other tetracycline antibiotic compounds. The tetracycline compound of the invention may be administered with a pharmaceutically acceptable carrier.

The language "effective amount" of the compound is that amount necessary or sufficient to treat or prevent a tetracycline compound responsive state. The effective amount can vary depending on such factors as the size and weight of the subject, the type of illness, or the particular tetracycline compound. For example, the choice of the tetracycline compound can affect what constitutes an "effective amount". One of ordinary skill in the art would be able to study the aforementioned factors and make the determination regarding the effective amount of the tetracycline compound without undue experimentation.

The invention also pertains to methods of treatment against microorganism infections and associated diseases. The methods include administration of an effective amount of one or more tetracycline compounds to a subject. The subject can be either a plant or, advantageously, an animal, e.g., a mammal, e.g., a human.

In the therapeutic methods of the invention, one or more tetracycline compounds of the invention may be administered alone to a subject, or more typically a compound of the invention will be administered as part of a pharmaceutical composition in mixture with conventional excipient, i.e., pharmaceutically acceptable organic or inorganic carrier substances suitable for parenteral, oral or other desired administration and which do not deleteriously react with the active compounds and are not deleterious to the recipient thereof.

In one embodiment, the pharmaceutical composition comprises a 7-substituted tetracycline compound of the invention, e.g., of formula I. In a further embodiment, the 7-substituted tetracycline compound is 7-phenyl sancycline, 7,9 diphenylsancycline, 7-(2-fluorophenyl) sancycline, 7-(2-chlorophenyl) sancycline, 7-(2-bromophenyl) sancycline, 742-iodophenyl) sancycline, 7-(3-fluorophenyl) sancycline, 7-(3-chlorophenyl) sancycline, 7-(3-bromophenyl) sancycline, 7-(3-iodophenyl) sancycline, 7-(4-fluorophenyl) sancycline, 7-(4-chlorophenyl) sancycline, 7-(4-bromophenyl) sancycline, 7-(4-iodophenyl) sancycline, 7-(4-trichloromethylphenyl) sancycline, 7-(4-trifluoromethylphenyl) sancycline, 7-(4-tribromomethylphenyl) sancycline, or 7-(4-triiodomethylphenyl) sancycline, 7-(2-aminophenyl) sancycline, 7-(2-nitrophenyl) sancycline, 7-(2-N,N,-dimethylaminophenyl) sancycline, 7-(2-N,N,-diethylaminophenyl) sancycline, 7-(2-N,N,-dipropylaminophenyl) sancycline, 7-(2-N,N,-dibutylaminophenyl) sancycline, 7-(3-aminophenyl) sancycline, 7-(3-nitrophenyl) sancycline, 7-(3-N,N,-dimethylaminophenyl) sancycline, 7-(3-N,N,-diethylaminophenyl) sancycline, 7-(3-N,N,-dipropylaminophenyl) sancycline, 7-(3-N,N,-dibutylaminophenyl) sancycline, 7-(4-aminophenyl) sancycline, 7-(4-nitrophenyl) sancycline, 7-(4-N,N,-dimethylaminophenyl) sancycline, 7-(4-N,N,-diethylaminophenyl) sancycline, 744-N,N,-dipropylaminophenyl) sancycline, and 7-(4-N,N,-dibutylaminophenyl) sancycline, where said compounds are substantially free of positional isomers.

The language "pharmaceutically acceptable carrier" includes substances capable of being coadministered with the tetracycline compound(s), and which allow both to perform their intended function, e.g., treat or prevent a tetracycline compound responsive state. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds of the invention.

The tetracycline compounds of the invention that are basic in nature are capable of forming a wide variety of salts with various inorganic and organic acids. The acids that may be used to prepare pharmaceutically acceptable acid addition salts of the tetracycline compounds of the invention that are basic in nature are those that form non-toxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,1'-methylene-bis-(2-hydroxy-3-naphthoate)] salts. Although such salts must be pharmaceutically acceptable for administration to a subject, e.g., a mammal, it is often desirable in practice to initially isolate a tetracycline compound of the invention from the reaction mixture as a pharmaceutically unacceptable salt and then simply convert the latter back to the free base compound by treatment with an. alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The preparation of other tetracycline compounds of the invention not specifically described in the foregoing experimental section can be accomplished using combinations of the reactions described above that will be apparent to those skilled in the art.

The preparation of other tetracycline compounds of the invention not specifically described in the foregoing experimental section can be accomplished using combinations of the reactions described above that will be apparent to those skilled in the art.

The tetracycline compounds of the invention that are acidic in nature are capable of forming a wide variety of base salts. The chemical bases that may be used as reagents to prepare pharmaceutically acceptable base salts of those tetracycline compounds of the invention that are acidic in nature are those that form non-toxic base salts with such compounds. Such non-toxic base salts include, but are not limited to those derived from such pharmaceutically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines. The pharmaceutically acceptable base addition salts of tetracycline compounds of the invention that are acidic in nature may be formed with pharmaceutically acceptable cations by conventional methods. Thus, these salts may be readily prepared by treating the tetracycline compound of the invention with an aqueous solution of the desired pharmaceutically acceptable cation and evaporating the resulting solution to dryness, preferably under reduced pressure. Alternatively, a lower alkyl alcohol solution of the tetracycline compound of the invention may be mixed with an alkoxide of the desired metal and the solution subsequently evaporated to dryness.

The preparation of other tetracycline compounds of the invention not specifically described in the foregoing experimental section can be accomplished using combinations of the reactions described above that will be apparent to those skilled in the art.

The tetracycline compounds of the invention and pharmaceutically acceptable salts thereof can be administered via either the oral, parenteral or topical routes. In general, these compounds are most desirably administered in effective dosages, depending upon the weight and condition of the subject being treated and the particular route of administration chosen. Variations may occur depending upon the species of the subject being treated and its individual response to said medicament, as well as on the type of pharmaceutical formulation chosen and the time period and interval at which such administration is carried out.

The pharmaceutical compositions of the invention may be administered alone or in combination with other known compositions for treating tetracycline responsive states in a mammal. Preferred mammals include pets (e.g., cats, dogs, ferrets, etc.), farm animals (cows, sheep, pigs, horses, goats, etc.), lab animals (rats, mice, monkeys, etc.), and primates (chimpanzees, humans, gorillas). The language "in combination with" a known composition is intended to include simultaneous administration of the composition of the invention and the known composition, administration of the composition of the invention first, followed by the known composition and administration of the known composition first, followed by the composition of the invention. Any of the therapeutically composition known in the art for treating tetracycline responsive states can be used in the methods of the invention.

The compounds of the invention may be administered alone or in combination with pharmaceutically acceptable carriers or diluents by any of the routes previously mentioned, and the administration may be carried out in single or multiple doses. For example, the novel therapeutic agents of this invention can be administered advantageously in a wide variety of different dosage forms, i.e., they may be combined with various pharmaceutically acceptable inert carriers in the form of tablets, capsules, lozenges, troches, hard candies, powders, sprays, creams, salves, suppositories, jellies; gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (including intraperitoneal, subcutaneous, intravenous, intradermal or intramuscular injection), solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are: suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Therapeutic compounds may be formulated in sterile form in multiple or single dose formats such as being dispersed in a fluid carrier such as sterile physiological saline or 5% saline dextrose solutions commonly used with injectables.

Additionally, it is also possible to administer the compounds of the present invention topically when treating inflammatory conditions of the skin. Examples of methods of topical administration include transdermal, buccal or sublingual application. For topical applications, therapeutic compounds can be suitably admixed in a pharmacologically inert topical carrier such as a gel, an ointment, a lotion or a cream. Such topical carriers include water, glycerol, alcohol, propylene-glycol, fatty alcohols, triglycerides, fatty acid esters, or mineral oils. Other possible topical carriers are liquid petrolatum, isopropylpalmitate, polyethylene glycol, ethanol 95%, polyoxyethylene monolaurate 5% in water, sodium lauryl sulfate 5% in water, and the like. In addition, materials such as anti-oxidants, humectants, viscosity stabilizers and the like also may be added if desired.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

In addition to treatment of human subjects, the therapeutic methods of the invention also will have significant veterinary applications, e.g. for treatment of livestock such as cattle, sheep, goats, cows, swine and the like; poultry such as chickens, ducks, geese, turkeys and the like; horses; and pets such as dogs and cats. Also, the compounds of the invention may be used to treat non-animal subjects, such as plants.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

In general, compounds of the invention for treatment can be administered to a subject in dosages used in prior tetracycline therapies. See, for example, the *Physicians' Desk Reference*. For example, a suitable effective dose of one or more compounds of the invention will be in the range of from 0.01 to 100 milligrams per kilogram of body weight of recipient per day, preferably in the range of from 0.1 to 50 milligrams per kilogram body weight of recipient per day, more preferably in the range of 1 to 20 milligrams per kilogram body weight of recipient per day. The desired dose is suitably administered once daily, or several sub-doses, e.g. 2 to 5 sub-doses, are administered at appropriate intervals through the day, or other appropriate schedule.

It will also be understood that normal, conventionally known precautions will be taken regarding the administration of tetracyclines generally to ensure their efficacy under normal use circumstances. Especially when employed for therapeutic treatment of humans and animals in vivo, the practitioner should take all sensible precautions to avoid conventionally known contradictions and toxic effects. Thus, the conventionally recognized adverse reactions of gastrointestinal distress and inflammations, the renal toxicity, hypersensitivity reactions, changes in blood, and impairment of absorption through aluminum, calcium, and magnesium ions should be duly considered in the conventional manner.

Furthermore, the invention also pertains to the use of a tetracycline compound of formula I which is substantially free of positional isomers, for the preparation of a medicament. The medicament may include a pharmaceutically acceptable carrier and the tetracycline compound is an effective amount, e.g., an effective amount to treat a tetracycline responsive state.

In yet another embodiment, the invention also pertains to the use of a tetracycline compound of formula I which is substantially free of positional isomers to treat a tetracycline responsive state, e.g., in a subject, e.g., a mammal, e.g., a human.

Compounds of the invention may be made as described below, with modifications to the procedure below within the skill of those of ordinary skill in the art.

Example 1

Synthesis of the 7-Substituted Tetracycline Compounds 7-iodosancycline

The following exemplary method allows the preparation of tetracycline compounds of the invention having a desired purity, e.g., such that the desired compound is provided substantially free of positional isomers. One gram of sancycline was dissolved in 25 mL of trifluoroacetic acid that was cooled to 0° C. (on ice). 1.2 equivalents of N-iodosuccinimide (NIS) was added to the reaction mixture and reacted for forty minutes. The reaction was removed from the ice bath and was allowed to react at room temperature for an additional five hours. The mixture was then analyzed by HPLC and TLC, was driven to completion by the stepwise addition of NIS. After completion of the reaction, the TFA was removed in vacuo and ~3 mL of MeOH was added to dissolve the residue. The methanolic solution was then added slowly to a rapidly stirring solution of diethyl ether to form a greenish brown precipitate. The 7-iodo isomer of sancycline is purified by treating the 7-iodo product with activated charcoal, filtering through Celite, and subsequent removal of the solvent in vacuo to produce the 7-isomer compound as a pure yellow solid in 75% yield.

MS (M+H) (formic acid solvent): 541.3

Rt: Hypersil C18 BDS Column, 11.73

$^1$H NMR: 300 MHz (Methanol $d_4$, TMS): δ 7.87-7.90 (d, 1H); 6.66-6.69 (d, 1H); 4.06 (s, 1H); 2.98 (s, 6H); 2.42 (m, 1H); 2.19 (m, 1H); 1.62 (m, 4H); 0.99 (m, 2H).

7-(3-nitrophenyl) sancycline 7-iodosancycline, 200 mg (0.28 mM), Pd(OAc)$_2$ 8.3 mg, and 10 mL of MeOH are added to a flask with a stir bar and the system degassed 3× using argon. Na$_2$CO$_3$ (117 mg) dissolved in water and argon degassed is added via syringe is added along with 3-nitrophenylboronic acid (75 mg) in MeOH that was also degassed. The reaction was followed by HPLC for 1 hour and cooled to room temperature. The solution was filtered, and dried to produce a crude mixture. The solid was dissolved in dimethylformamide and injected onto a preparative HPLC system using C18 reverse-phase silica. The fraction at 48-50 minutes was isolated, and the solvent removed in vacuo to yield the product plus salts. The salts were removed by extraction into 50:25:25 water:butanol:Ethyl acetate and dried in vacuo. This solid was dissolved in MeOH and the HCl salt made by bubbling in HCl gas. The solvent was removed to produce the product, substantially free of positional isomers, in 42% yield as a yellow solid.

7-(3-nitrophenyl) sancycline: Rt 16.3 min: MS (M+H, formic acid solvent): 536.4

114 NMR (Methanol d4-300 MHz). 5 8.1-8.2 (m, 2H), 7.10-7.15 (m, 1H), 7.68, (m, 4H), 4.05 (s, 1H), 3.79 (s, 2H), 3.05 (s, 6H), 2.43 (m, 2H), 1.61 (m, 4H), 1.05 (m, 2H)

7-(3-aminophenyl) sancycline 7-iodosancycline, 200 mg (0.37 mM), Pd(OAc)2 8.3 mg, and 10 mL of MeOH are added to a flask with a stir bar and the system degassed 3× using argon. Triethylamine (103 µL) is dispensed into the reaction flask via syringe and argon degassed. The 4-aminophenyl boronic acid (128 mg) dissolved in degassed DMF (2 mL) is added via syringe. The reaction was followed by HPLC for 18 hours and cooled to room temperature. The solution was filtered, and dried to produce a crude mixture. The solid was dissolved in dimethylformamide and injected onto a preparative HPLC system using C18 reverse-phase silica. The fraction at 14 7 minutes was isolated, and the solvent removed in vacuo to yield the product plus salts. The salts were removed by extraction into 50:25:25 water:butanol:ethyl acetate and dried in vacuo. This solid was dissolved in MeOH and the HCl salt made by bubbling in HCl gas. The solvent was removed to produce the product, substantially free of positional isomers, in low yield as a yellow solid.

7-(3-aminophenyl) sancycline: Rt 4.3 min: MS (M+H, formic acid solvent): 506.2

7-(4-N,N-dimethylaminophenyl) sancycline 7-iodosancycline, 600 mg (0.92 mM), Pd(OAc)2 30 mg, and 20 mL of MeOH are added to a flask with a stir bar and the system degassed 3× using argon. Triethylamine (300 µl) was added via syringe is added along with 4-N,N-dimethylaminophenylboronic acid (303 mg, 1.83 mM) in MeOH that was also degassed. The reaction was followed by HPLC for 2 hours and cooled to room temperature. The solution was filtered, and dried to produce a crude mixture. The solid was dissolved in dimethylformamide and injected onto a preparative HPLC system using CI8 reverse-phase silica. The fraction at 17 minutes was isolated, and the solvent removed in vacuo to yield the product plus salts. The salts were removed by extraction into 50:25:25 water, butanol, ethyl acetate and dried in vacuo. This solid was dissolved in MeOH and the HCl salt made by bubbling in HCl gas. The solvent was removed to produce the product, substantially free of positional isomers, in 57% yield as a yellow solid.

7-(4-N,N-dimethylaminophenyl) sancycline: Rt 7.55 min: MS (M+H, formic acid solvent): 534.2

$^1$H NMR (Methanol d$_4$-300 MHz) δ 7.02-7.05 (d, 1H), 7.79-7.82 (d, 1H), 7.49-7.63 (m, 4H), 4.10 (s, 1H), 3.25-3.40 (br m, 12H), 2.58-2.70 (m, 2H), 1.61 (m, 4H), 1.00 (m, 2H).

7-phenylsancycline 7-iodosancycline, 150 mg (0.28 mM), Pd(OAc)$_2$ and 10 mL of MeOH are added to a flask with a stir bar and the system degassed 3× using argon. Na$_2$CO3 (87 mg, 0.8 mM) dissolved in water and argon degassed is added via syringe is added along with phenylboronic acid (68 mg, 0.55 mM) in MeOH that was also degassed. The reaction was followed by HPLC for 2 hours and cooled to room temperature. The solution was filtered, and dried to produce a crude mixture. The solid was dissolved in dimethylformamide and injected onto a preparative HPLC system using C18 reverse-phase silica. The fraction at 36-38 minutes was isolated, and the solvent removed in vacuo to yield the product plus salts. The salts were removed before extraction into 50:25:25 water:butanol:ethyl acetate and dried in vacuo. This solid was dissolved in MeOH and the HCl salt made by bubbling in HCl gas. The solvent was removed to produce the product, substantially free of positional isomers, in 42% yield as a yellow solid.

7-phenyl sancycline: Rt 21.6 min: MS (M+H, formic acid solvent): 491.3

$^1$H NMR (Methanol d$_4$-300 MHz) δ 7.87 (d, J=8.86 Hz, 1H), 7.38 (m, 5H), 6.64 (d, 8.87 Hz, 1H), 4.00 (s, 1H), 3.84 (s, 2H), 3.01 (s, 6H), 2.46 (m, 2H), 1.63 (m, 4H), 0.95 (m, 2H)

7-(4-chlorophenyl)sancycline 7-iodosancycline, 500 mg (0.91 mM), Pd(OAc)$_2$ 21 mg, and 20 mL of MeOH are added to a flask with a stir bar and the system degassed 3× using argon. Na$_2$CO$_3$ (293 mg, 2.8 mM) dissolved in water and argon degassed, is added via syringe is added along with 4-Cl-phenylboronic acid (289 mg, 1.85 mM) in MeOH that was also degassed. The reaction was followed by HPLC for 45 minutes and cooled to room temperature. The solution was filtered, and dried to produce a crude mixture. The solid was dissolved in dimethylformamide and injected onto a preparative HPLC system using C18 reverse-phase silica. The fraction at 39 minutes was isolated, and the solvent removed in vacuo to yield the product plus salts. The salts were removed by extraction into 50:25:25 water:butanol:ethyl acetate, and dried in vacuo. This solid was dissolved in MeOH and the HCl salt made by bubbling in HCl gas. The solvent was removed to produce the product, substantially free of positional isomers, in 57% yield as a yellow solid.

7-(4-chlorophenyl)sancycline: Rt 20.3 min: MS (M+H, formic acid solvent): 525.7

$^1$HNMR (Methanol d$_4$-300 MHz) δ 7.49-7.52 (d, J=8.54 Hz, 1H), 6.99¬7.01 (d, 8.61 Hz, 1H), 4.12 (s, 11-1), 3.67 (m, 111), 3.06 (s, 6H), 2.58 (m, 21-1), 1.62 (m, 411), 1.01 (m, 2H)

7-(4-fluorophenyl)sancycline 7-iodosancycline, 200 mg (0.3 mM), Pd(OAc)$_2$ 8.3 mg, and 10 mL of MeOH are added to a flask with a stir bar and the system degassed 3× using argon. Na$_2$CO$_3$ (104 mg, 1.1 mM) dissolved in water and argon degassed is added via syringe is added along with 4-F¬phenylboronic acid (104 mg, 0.7 mM) in MeOH that was also degassed. The reaction was followed by HPLC for 20 minutes and cooled to room temperature. The solution was filtered, and dried to produce a crude mixture. The solid was dissolved in dimethylformamide and injected onto a preparative HPLC system using C18 reverse-phase silica. The fraction at 19-20 minutes was isolated, and the solvent removed in vacuo to yield the product plus salts. The salts were removed by extraction into 50:25:25 water:butanol:ethyl acetate and dried in vacuo. This solid was dissolved in MeOH and the HCl salt made by bubbling in HCl gas. The solvent was removed to produce the product, substantially free of positional isomers, in 47% yield as a yellow solid.

7-(4-fluorophenyl)sancycline: Rt 19.5 min: MS (M+H, formic acid solvent): 509.4

1H NMR (Methanol d$_4$-300 MHz) δ 6.92-6.95 (d, 111), 7.45-7.48 (d, 1H), 7.15-7.35 (m, 4H), 4.05 (s, 114), 3.62 (m, 111), 3.08 (s, 6H), 2.55 (m, 2H), 1.65 (m, 4H), 1.00 (m, 2H)

Example 2

In Vitro Minimum Inhibitory Concentration (MIC) Assay

The following assay is used to determine the efficacy of tetracycline compounds against common bacteria. 2 mg of each compound is dissolved in 100 µl of DMSO. The solution is then added to cation-adjusted Mueller Hinton broth (CAMHB), which results in a final compound concentration of 200 µg per ml. The tetracycline compound solutions are diluted to 50 µl volumes, with a test compound concentration of 0.098 µg/ml. Optical density (OD) determinations are made from fresh log-phase broth cultures of the test strains. Dilutions are made to achieve a final cell density of $1 \times 10^6$ CFU/ml. At OD=1, cell densities for different genera should be approximately:

| | |
|---|---|
| *E. coli* | 1 × 10⁹ CFU/ml |
| *S. aureus* | 5 × 10⁸ CFU/ml |
| *Enterococcus* sp. | 2.5 × 10⁹ CFU/ml |

50 μl of the cell suspensions are added to each well of microtiter plates. The final cell density should be approximately 5×10⁵ CFU/ml. These plates are incubated at 35° C. in an ambient air incubator for approximately 18 hr. The plates are read with a microplate reader and are visually inspected when necessary. The MIC is defined as the lowest concentration of the tetracycline compound that inhibits growth. Compounds of the invention indicate good inhibition of growth.

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

The invention claimed is:

1. A method for preparing a 7-substituted tetracycline compound at least 75% free of positional isomers, comprising:
   (a) reacting an unsubstituted tetracycline compound with at least one equivalent of N-iodosuccinimide in trifluoroacetic acid to result in a 7-iodo tetracycline compound at least 75% free of positional isomers;
   (b) reacting the 7-iodo tetracycline compound with a boronic acid, a palladium catalyst and aqueous sodium carbonate in a solvent; and
   (c) purifying the resultant solution from step (b).

2. The method of claim 1, wherein the unsubstituted tetracycline compound is sancycline.

3. The method of claim 1, wherein the boronic acid is a phenylboronic acid.

4. The method of claim 1, wherein the palladium catalyst is Pd(OAc)₂.

5. The method of claim 1, wherein the 7-iodo tetracycline compound is at least 80% free of positional isomers.

6. The method of claim 1, wherein the 7-iodo tetracycline compound is at least 90% free of positional isomers.

7. The method of claim 1, wherein the 7-iodo tetracycline compound is at least 95% free of positional isomers.

8. The method of claim 1, wherein the boronic acid is selected from the group consisting of: 3-nitrophenyl boronic acid, 4-aminophenyl boronic acid, 4-N,N-dimethylaminophenyl boronic acid, phenylboronic acid, 4-Cl-phenylboronic acid and 4-F-phenylboronic acid.

9. A method for preparing a 7-substituted tetracycline compound at least 75% free of positional isomers, comprising:
   (a) reacting an unsubstituted tetracycline compound with at least one equivalent of N-iodosuccinimide in trifluoroacetic acid to result in a 7-iodo tetracycline compound at least 75% free of positional isomers;
   (b) reacting the 7-iodo tetracycline compound with a tin reagent, a palladium catalyst and, optionally, copper iodide; and
   (c) purifying the resultant solution from step (b).

10. The method of claim 9, wherein the unsubstituted tetracycline compound is sancycline.

11. The method of claim 9, wherein the tin reagent is a SnBu₃ reagent.

12. The method of claim 9, wherein the palladium catalyst is selected from the group consisting of: Pd(PPh₃)₂Cl₂ and Pd(AsPh₃)₂Cl₂.

13. The method of claim 9, wherein the 7-iodo tetracycline compound is at least 80% free of positional isomers.

14. The method of claim 9, wherein the 7-iodo tetracycline compound is at least 90% free of positional isomers.

15. The method of claim 9, wherein the 7-iodo tetracycline compound is at least 95% free of positional isomers.

* * * * *